US00PP18334P3

(12) United States Plant Patent
Korlipara

(10) Patent No.: US PP18,334 P3
(45) Date of Patent: Dec. 18, 2007

(54) *COREOPSIS* PLANT NAMED 'CHERRY LEMONADE'

(50) Latin Name: *Coreopsis*
Varietal Denomination: Cherry Lemonade

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 17 days.

(21) Appl. No.: 11/343,832

(22) Filed: Jan. 30, 2006

(65) Prior Publication Data

US 2007/0180591 P1 Aug. 2, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Coreopsis* plant named 'Cherry Lemonade' characterized by yellow foliage, red flowers, and a dwarf habit.

1 Drawing Sheet

Botanical designation: *Coreopsis* hybrid (parents unknown).

Variety denomination: 'Cherry Lemonade'.

Cross reference to: co-pending applications for *Coreopsis* 'Pink Lemonade' (U.S. application No. 11/343,831 and 'Strawberry Lemonade' (U.S. application No. 11/344,356).

BACKGROUND OF THE INVENTION

The present invention relates to a new and distinct plant of *Coreopsis* and given the cultivar name 'Cherry Lemonade'. *Coreopsis* is in the family Asteraceae. This new cultivar originated from offspring located at the nursery in Canby, Oreg. and reproduced in tissue culture where further selections were made. This selection was made for its cherry red flowers.

SUMMARY OF THE INVENTION

The following traits have been repeatedly observed and are determined to be the unique characteristics of 'Cherry Lemonade'. These characteristics in combination distinguish 'Cherry Lemonade' as a new and distinct cultivar:

1. Golden yellow foliage.
2. Unique red daisy type flowers.
3. Dwarf mounding habit.
4. Very free flowering.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Cherry Lemonade' growing in the ground in the field in August in Canby, Oreg.

DETAILED PLANT DESCRIPTION

The following is a detailed description of the new *Coreopsis* cultivar based on observations of a one-year-old specimen grown in a container in the greenhouse over the winter and then planted on May 1$^{st}$ in the ground in the trail fields in full sun. The data was taken in August from this material. The trial fields are under typical outdoor conditions in Canby, Oreg. Canby in Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 9 to 10.
- *Size.*—40 cm wide and 25 cm tall to top of flowers.
- *Form.*—Low mound with freely branching stems.
- *Vigor.*—Excellent.
- *Roots.*—Fibrous, freely branching, fine and white in color. Roots develops easily from cuttings.

Stem:
- *Type.*—Ascending.
- *Size.*—20 cm tall and 1 to 2 mm wide.
- *Internode length.*—12 to 30 mm.
- *Surface.*—Glabrous.
- *Color.*—Yellow Green 146C.

Leaf:
- *Type.*—Simple.
- *Shape.*—Linear.
- *Arrangement.*—Opposite.
- *Length.*—25 to 40 mm, sessile.
- *Width.*—1 to 2 mm.

*Margins.*—Entire.

*Apex.*—Acute.

*Base.*—Attenuate.

*Surface texture.*—Glabrous, soft and smooth to the touch.

*Venation.*—Pinnate.

*Color.*—Top side — Yellow, Yellow 10A with a green main vein Yellow Green 146C to Yellow Green 146A where shaded. Bottom — same as top side.

Inflorescence:

*Type.*—Long stalked terminal heads of daisy type flowers.

*Peduncle.*—7 cm tall and 1 mm wide, glabrous, Yellow 10A to Yellow Green 146C where shaded.

*Bud.*—Oval in shape, 3.5 mm long and 3 mm wide, glabrous, Green 147A on the bottom half, Greyed Yellow 161A on top half with Greyed Red 183A at the tip and in the seams.

*Size.*—2.5 to 3.5 cm wide and 8 mm deep.

*Ray florets.*—No pistil or stamen. Number — 8. Shape: Obovate with the tip three toothed with tooth's obtuse, base attenuate. Size: Grows to 17 mm long, 8 mm wide. Surface texture: glabrous, soft and velvety to the touch. Color: Ray floret, topside — Closest to 59A but deeper in color. Ray, bottom side — Greyed Purple 187B.

*Disc.*—Shape: Conic, deeper with maturity. Size: 7 mm wide and becoming 5 mm deep with maturity. Color: Brown 200B when in bud, opening to orange, Orange 24A with a dark background, Greyed Purple 187A.

*Disc florets.*—About 45 in number, 5 mm long and 1 mm wide, tubular, 4 lobed, Greyed Purple 187A at the apex to Orange 24A in middle and Yellow Orange 20B near base. Pistil — 1 in number, 6 mm long, Orange 24A overall, extruding) 2-branched stigma, ovary 1.5 mm long, style 4 mm long. Stamen — 4, filaments 3 mm long, extruding, Black 202A. Pollen color — Yellow 12C.

*Phyllaries.*—In two series, inner series opaque, 8 in number, rotate, Green 148A on the bottom half, Greyed Orange 164B on top half, each 4 mm long and 1.5 mm wide, ovate lanceolate, acute, entire, glabrous; outer series leafy, usually 5 in number, campanulate, each lobe 1.5 mm long and 1 mm wide, Yellow Green 147A with clear margins, ovate, entire, acute, glabrous.

*Receptacle.*—Green 147A, conic, 2 mm long, and 2 mm wide, glabrous.

*Bloom period.*—June through September in Canby, Oreg.

*Fragrance.*—Light, daisy like.

*Lastingness.*—Each bloom lasts about five days.

Seed: None produced.

*Fertility.*—Infertile.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant Pat. No. 15,455), this new cultivar has the same flower size but has red flowers rather than rose, a much shorter habit, and yellow foliage rather than green.

I claim:

1. A new and distinct *Coreopsis* plant as herein illustrated and described.

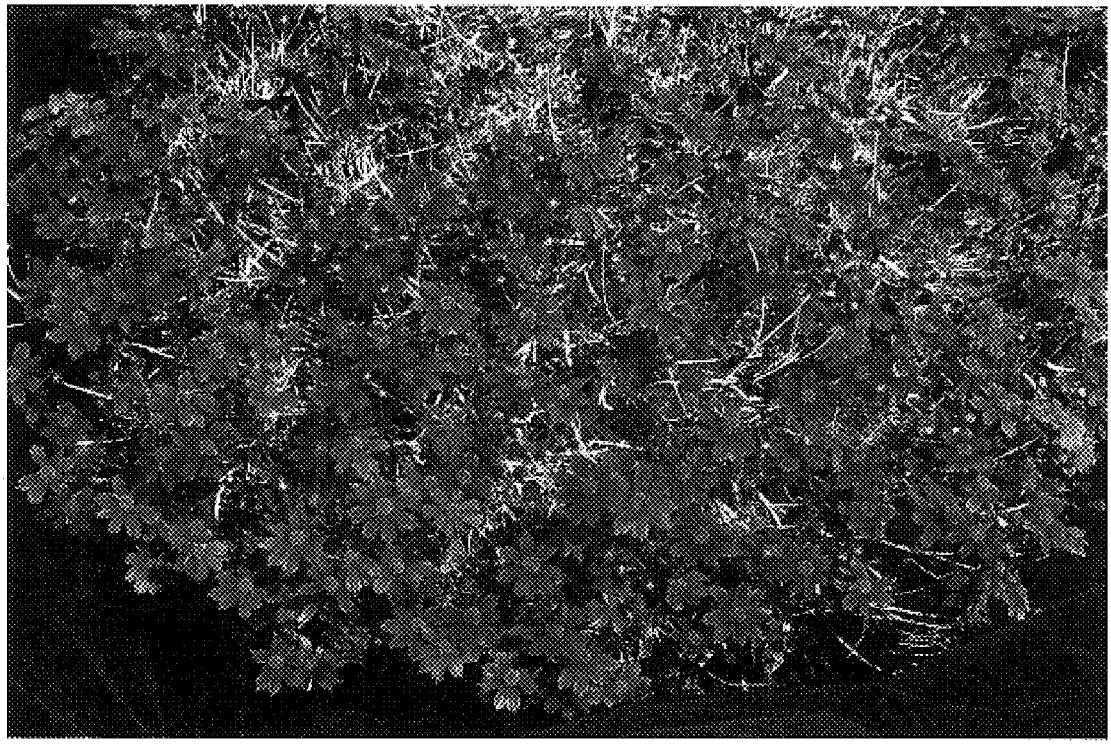

* * * * *